(12) United States Patent
Almodovar

(10) Patent No.: US 12,653,524 B2
(45) Date of Patent: Jun. 16, 2026

(54) SUTURING DEVICE

(71) Applicant: Ergosurgical Group Corp., Santa Maria, PR (US)

(72) Inventor: Luis Jose Almodovar, Santa Maria, PR (US)

(73) Assignee: Ergosurgical Group Corp., Santa Maria, PR (US)

( * ) Notice: Subject to any disclaimer, the term of this patent is extended or adjusted under 35 U.S.C. 154(b) by 279 days.

(21) Appl. No.: 18/269,736

(22) PCT Filed: Oct. 22, 2021

(86) PCT No.: PCT/US2021/056325
§ 371 (c)(1),
(2) Date: Jun. 26, 2023

(87) PCT Pub. No.: WO2022/087467
PCT Pub. Date: Apr. 28, 2022

(65) Prior Publication Data
US 2024/0057996 A1 Feb. 22, 2024

Related U.S. Application Data

(60) Provisional application No. 63/104,503, filed on Oct. 22, 2020.

(51) Int. Cl.
A61B 17/04 (2006.01)
A61B 17/06 (2006.01)
A61B 17/00 (2006.01)

(52) U.S. Cl.
CPC ...... A61B 17/0482 (2013.01); A61B 17/0469 (2013.01); A61B 17/06066 (2013.01); *A61B 2017/00389* (2013.01)

(58) Field of Classification Search
CPC ........... A61B 17/0482; A61B 17/0483; A61B 17/0491; A61B 17/0469; A61B 17/06066; A61B 2017/00389
See application file for complete search history.

(56) References Cited

U.S. PATENT DOCUMENTS 5,540,705 A * 7/1996 Meade ............... A61B 17/0491
606/147
7,004,951 B2 2/2006 Gibbens, III
(Continued)

FOREIGN PATENT DOCUMENTS

CN 102300507 12/2011
CN 102405022 4/2012
(Continued)

OTHER PUBLICATIONS

International Search Report and Written Opinion dated Feb. 3, 2022 in related International Application No. PCT/US2021/056325 filed Oct. 22, 2021 (11 pages).
(Continued)

*Primary Examiner* — Tuan V Nguyen
(74) *Attorney, Agent, or Firm* — Dentons US LLP

(57) ABSTRACT

Disclosed is a device, comprising a handle, a rotatable shaft, a sleeve comprising a first curved, hollow, stainless steel (magnetized) tube and a second curved, hollow, stainless steel (magnetized) tube, wherein the first tube is positioned on a first side of the shaft and the second tube is positioned on a second side of the shaft, wherein the first tube comprises a sharp tip and the second tube comprises a sharp tip, with a reciprocating shuttle and a curved needle positioned in the sleeve, wherein the sleeve having an inner diameter large enough to accommodate the needle and shuttle, and wherein the shuttle is positioned between the sleeve and the
(Continued)

needle. Rotation of the shaft moves the shuttle which in turn moves the needle through the sleeve.

16 Claims, 12 Drawing Sheets

(56)                    References Cited

U.S. PATENT DOCUMENTS

| | | | |
|---|---|---|---|
| 2002/0193809 A1* | 12/2002 | Meade ............... | A61B 17/0469 606/222 |
| 2003/0083674 A1 | 5/2003 | Gibbens | |
| 2006/0282094 A1 | 12/2006 | Stokes | |
| 2010/0042116 A1 | 2/2010 | Chui | |
| 2015/0127024 A1 | 5/2015 | Berry | |
| 2020/0078007 A1 | 3/2020 | O'Hara | |

FOREIGN PATENT DOCUMENTS

| | | |
|---|---|---|
| DE | 2025534 | 12/1971 |
| EP | 3476302 | 5/2019 |
| JP | H07178100 | 7/1995 |

OTHER PUBLICATIONS

China Office Action dated Jan. 9, 2026 in related Application 202180081352.2 filed Oct. 22, 2021 (4 pages).

* cited by examiner

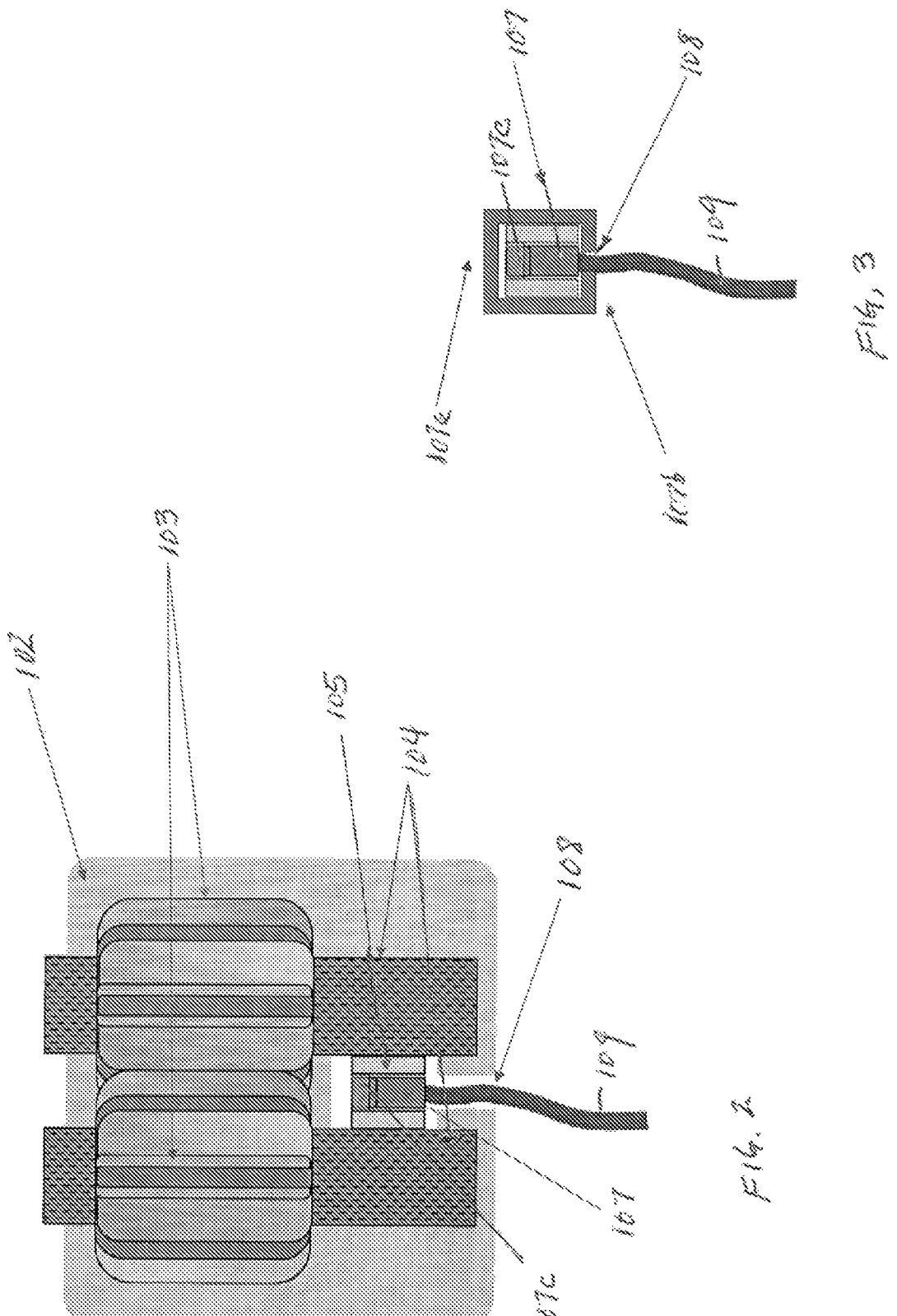

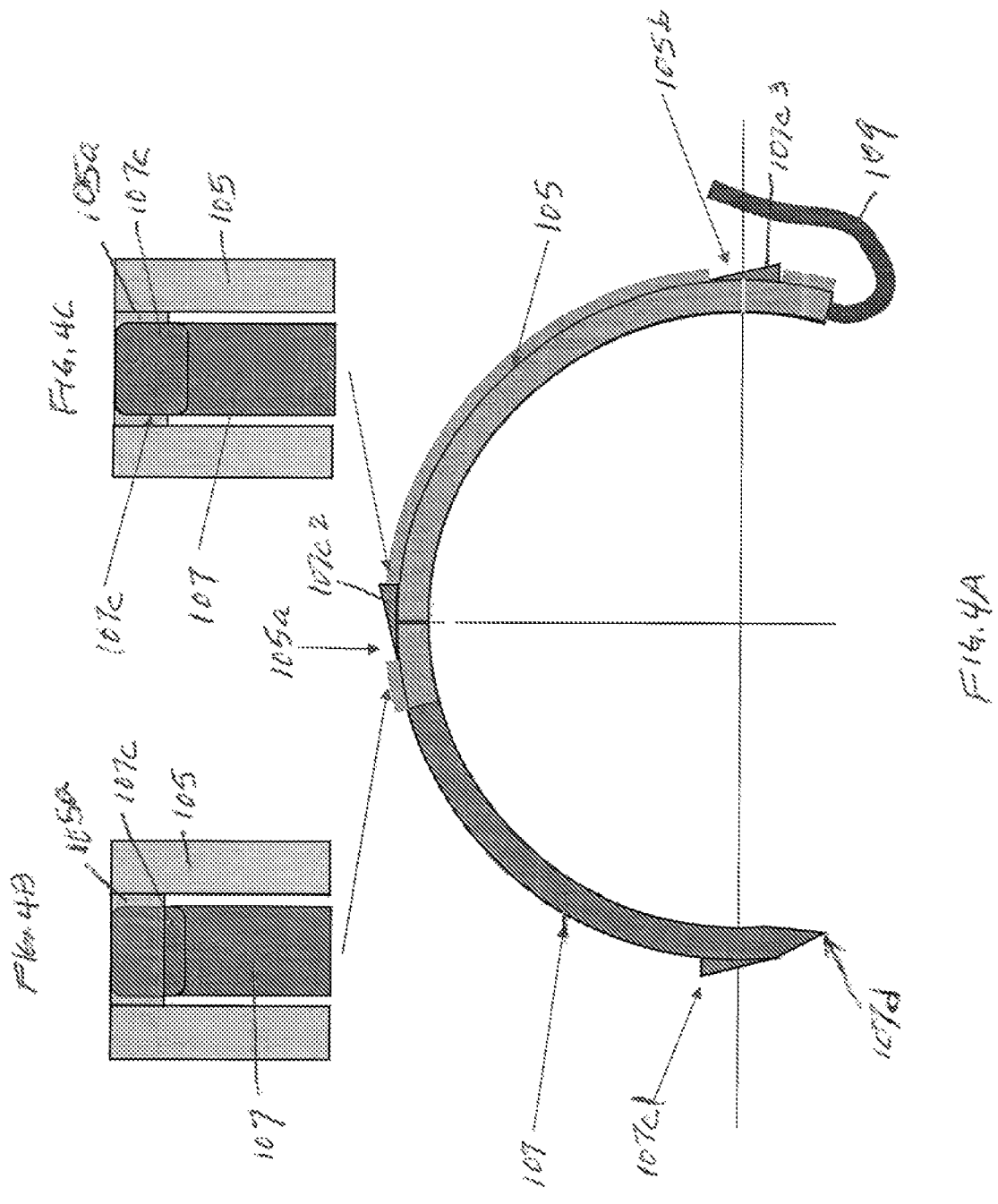

SUTURING DEVICE

CROSS REFERENCE TO RELATED APPLICATIONS

This patent application claims the benefit of priority to PCT International Application No. PCT/US19/25645, filed 3 Apr. 2019; which claims the benefit of U.S. Provisional Patent Application 63/104,503, filed Oct. 22, 2020, each of which is incorporated by reference herein for all purposes.

TECHNICAL FIELD

The present disclosure generally relates to suture devices and methods.

BACKGROUND

Suturing procedures used to close wounds or incisions consume a considerable amount of time during a surgical procedure. Generally, the instruments used in suturing procedures are the suturing material, the suturing needle, and the suturing driver. Efforts have been made to reduce the time and enhance the safety of the procedure.

Direct contact between the rollers, or other driving mechanism, with the needle has generally been pursued. Although intuitive, this approach presents several challenges in terms of achieving the desired tissue depth, needle size and the necessary complexity to move the needle.

Accordingly, new suturing device designs that actuate the suture needle in indirect manner are desirable and an object of the present disclosure.

SUMMARY

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e., that it will be taken to mean an inclusion of not only the listed components it directly references, but also other non-specified components or elements. This rationale will also be used when the term 'comprised' or 'comprising' is used in relation to one or more steps in a method or process.

The present disclosure provides, in one embodiment, a device comprising: a) a housing with a top end and a bottom end, and a first side and a second side, wherein the bottom end of the housing defines an opening; b) a first rotatable shaft with a first end and a second end, the first rotatable shaft coupled to a first roller gear proximal to the second end of the first rotatable shaft, the first roller gear and the second end of the first rotatable shaft positioned in the housing; c) a second rotatable shaft with first end and a second end, the second rotatable shaft coupled to a second roller gear proximal to the second end of the second rotatable shaft, the second roller gear and the second end of the second rotatable shaft positioned in the housing, wherein the first roller gear engages the second roller gear; d) a sleeve comprising a first curved, hollow, stainless steel, magnetized tube having a first end and a second end, the first end of the first tube having a first sharp tip, wherein the second end of the first tube is positioned on the first side of the housing, and a second curved, hollow, stainless steel, magnetized tube having a first end and a second end, the first end of the second tube having a second sharp tip, wherein the second end of the second tube is positioned on the second side of the housing; e) a reciprocating shuttle positioned in the sleeve; and f) a curved stainless steel, magnetized needle, positioned in the sleeve, wherein the sleeve having an inner diameter large enough to accommodate the needle and the shuttle, and wherein the shuttle is positioned between the sleeve and the needle, wherein the shuttle engages the needle, wherein the shuttle is coupled to the first and second rotatable shaft, and wherein a rotation of the first and second rotatable shaft moves the shuttle through the sleeve which in turn drives the needle through the sleeve.

In certain embodiments the needle comprises a first end, a second end and a middle portion, wherein the first end has a sharp tip and the second end is coupled to a suture. In some embodiments the needle comprises a plurality of fins. In other embodiments the needle comprises a first fin located proximal to the first end of the needle, a second fin proximal to the middle portion of the needle, and a third fin proximal to the second end of the needle. In yet other embodiments the second fin is located approximately 90 degrees from the first and third fins.

In additional embodiments the shuttle has a first end and a second end, and a first window proximal to the first end and a second window proximal to the second end. In certain embodiments the shuttle engages the needle via the interaction of the first or second window with the first, second or third fin. In some embodiments the sleeve is semicircular and extends greater than 180 degrees. In other embodiments the sleeve extends 210 degrees. In further embodiments the sleeve guides the needle through a 360 degree rotation through the sleeve. In particular embodiments the needle is semicircular and extends greater than 180 degrees. In certain embodiments the needle extends 210 degrees.

In certain embodiments the device further comprised a knob coupled to either the first roller gear or the second roller gear. In some embodiments the device further comprises a handle coupled to the knob.

The present disclosure also provides, in one embodiment, a method for suturing tissue, comprising the steps of: a) providing a device comprising: i) a handle; ii) a housing with a top end and a bottom end, and a first side and a second side, wherein the bottom end of the housing defines an opening; iii) a rotatable shaft with a first end and a second end, the rotatable shaft coupled to a first roller gear proximal to the second end of the rotatable shaft, the first roller gear and the second end of the rotatable shaft positioned in the housing, the rotatable shaft coupled to the handle; iv) a second roller gear positioned in the housing and engaged with the first roller gear; v) a sleeve comprising a first curved, hollow, stainless steel, magnetized tube and a second curved, hollow, stainless steel, magnetized tube, wherein the first tube is positioned on a first side of the shaft and the second tube is positioned on a second side of the shaft, wherein the first tube comprises a first sharp tip and the second tube comprises a second sharp tip; vi) a reciprocating shuttle; and vii) a curved stainless steel, magnetized needle, positioned in the sleeve, wherein the sleeve having an inner diameter large enough to accommodate the needle and the shuttle, and wherein the shuttle is positioned between the sleeve and the needle, wherein the shuttle engages the needle, wherein the shuttle is coupled to the shaft, and wherein a rotation of the shaft moves the shuttle which in turn drives the needle through the sleeve; b) piercing the tissue with the sleeve; c) actuating the rotatable shaft in the forward direction to advance the shuttle in the first tube of the sleeve which advances the needle into the tissue; d) actuating the rotatable shaft in the opposite direction to retract the shuttle into the second tube of the sleeve; e) repeating steps c) and d) until the needle is positioned in the starting position within the sleeve; and f) repeating steps b) through e) until completion of the suturing process. In certain embodiments the device further comprises a knob in communication with either the first roller gear or the second roller gear, the knob coupled to the handle.

The system as described herein, both as to its configuration and its mode of operation will be best understood, and additional objects and advantages thereof will become apparent, by the following detailed description of an embodiment taken in conjunction with the accompanying drawings.

When the word "invention" is used in this specification, the word "invention" includes "inventions", that is, the plural of "invention". By stating "invention", the Applicant does not in any way admit that the present application does not include more than one patentable and non-obviously distinct invention and Applicant maintains that the present application may include more than one patentably and non-obviously distinct invention. The Applicant hereby asserts that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the full scope of the application, which is measured by the claims, nor is it intended to be limiting as to the scope of the disclosure in any way.

BRIEF DESCRIPTION OF THE DRAWINGS

All of the figures depict preferred embodiments although other embodiments are contemplated, and the present disclosure is not limited to the embodiments shown.

FIG. 2 is an illustration of a side view of the housing and roller section shown in FIG. 1.

FIG. 3 is an illustration of a side view of the tissue-piercing needle shown in FIG. 1.

FIG. 4A, FIG. 4B and FIG. 4C are illustrations of a suture needle and reciprocating shuttle according to one embodiment of the present disclosure. FIG. 4A shows a forward view of the suture needle with needle tip at one end of the needle and a suture thread attached to the other end of the needle, with three fins 90 degrees apart from each other, and the reciprocating shuttle with front window and back window that engage the fins of the suture needle. FIG. 4B shows a cross-section view in front of the front window of the reciprocating shuttle, and FIG. 4C shows a cross-section view at the front window of the reciprocating shuttle.

Figure 5:
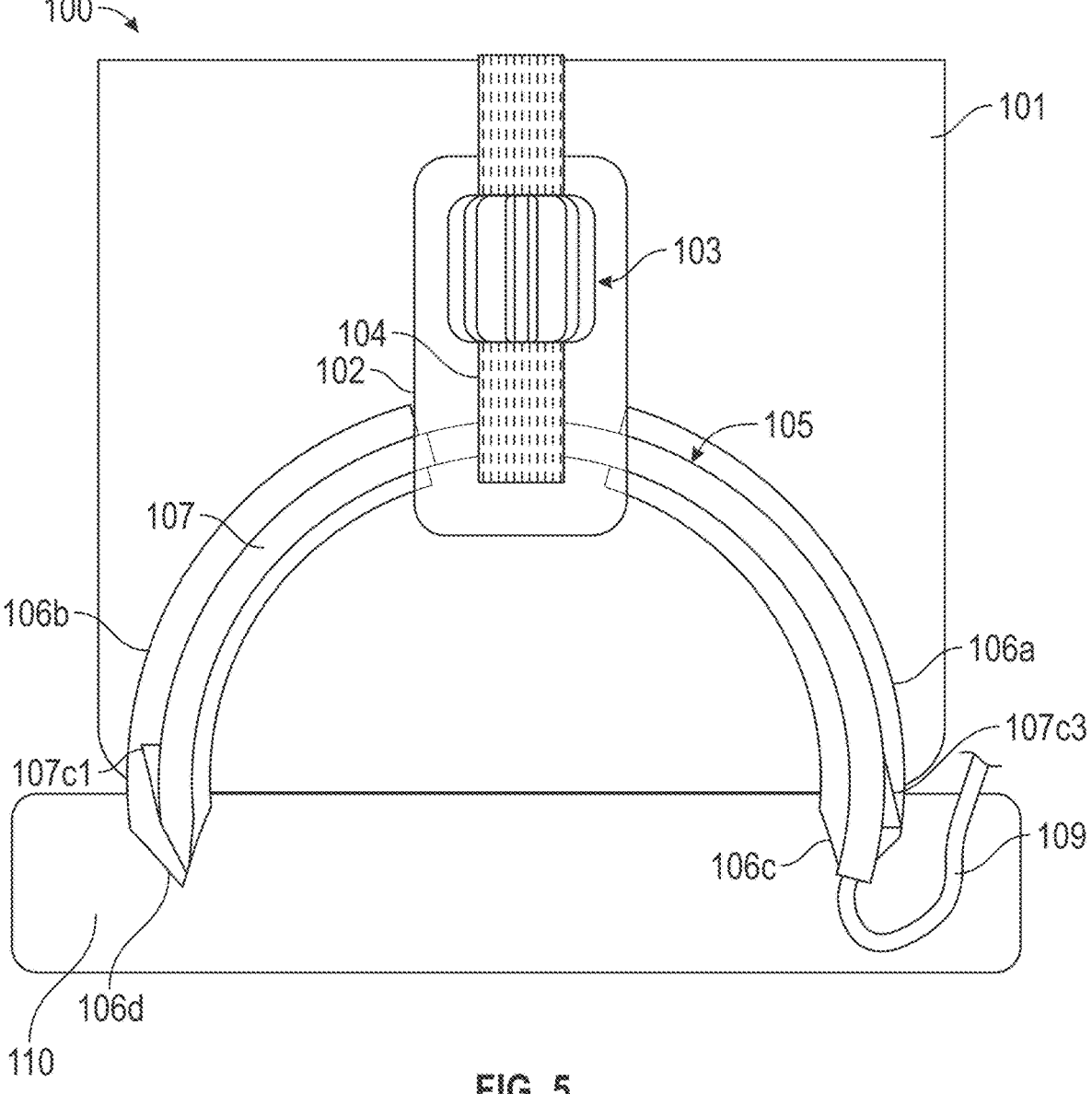

FIG. 5 is an illustration of a frontal view of a suturing device according to one embodiment of the present disclosure upon advancement into the tissue to be sutured. The suture needle and reciprocating shuttle are in the initial position.

Figure 6:
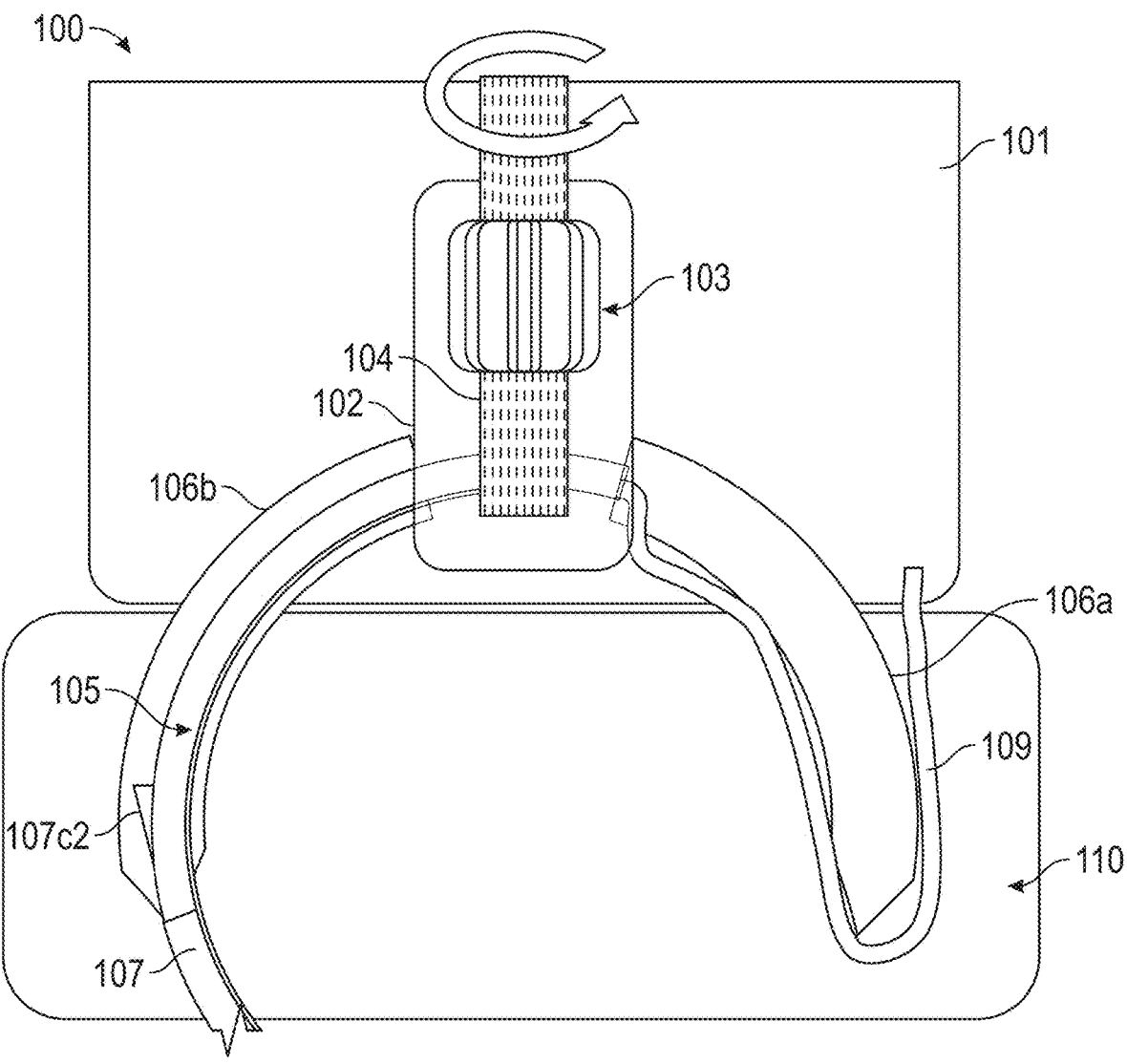

FIG. 6 is an illustration of a frontal view of the suturing device shown in FIG. 5. The wire rollers are rotated in the forward direction advancing the reciprocating shuttle 90 degrees to the second position of the reciprocating shuttle, driving the suture needle into the tissue to be sutured.

Figure 7:
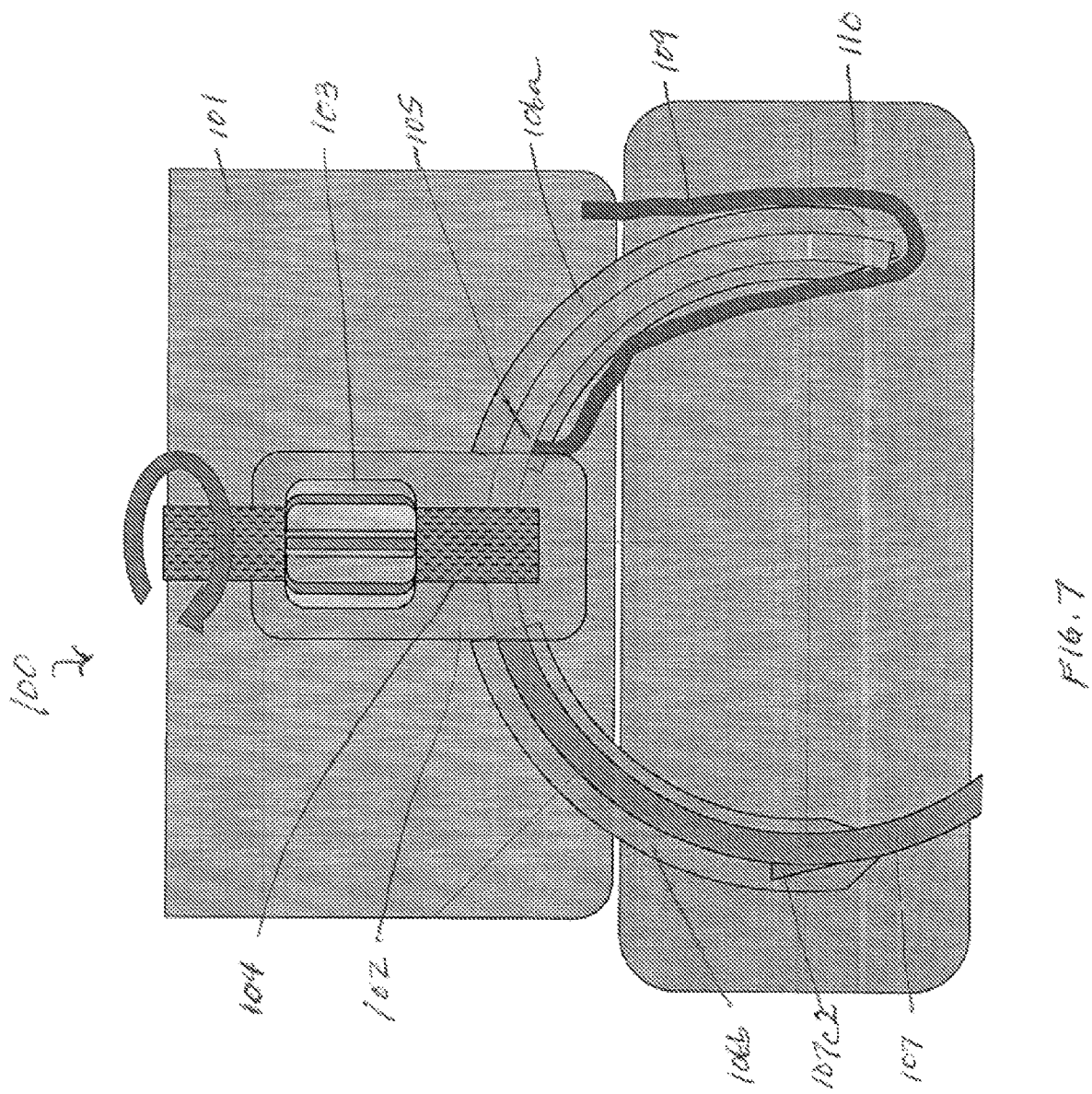

FIG. 7 is an illustration of a frontal view of the suturing device shown in FIG. 6. The wire rollers are rotated in the backward direction, moving the reciprocating shuttle back 90 degrees to the initial position of the reciprocating shuttle, with the suturing needle remaining in place.

Figure 8:
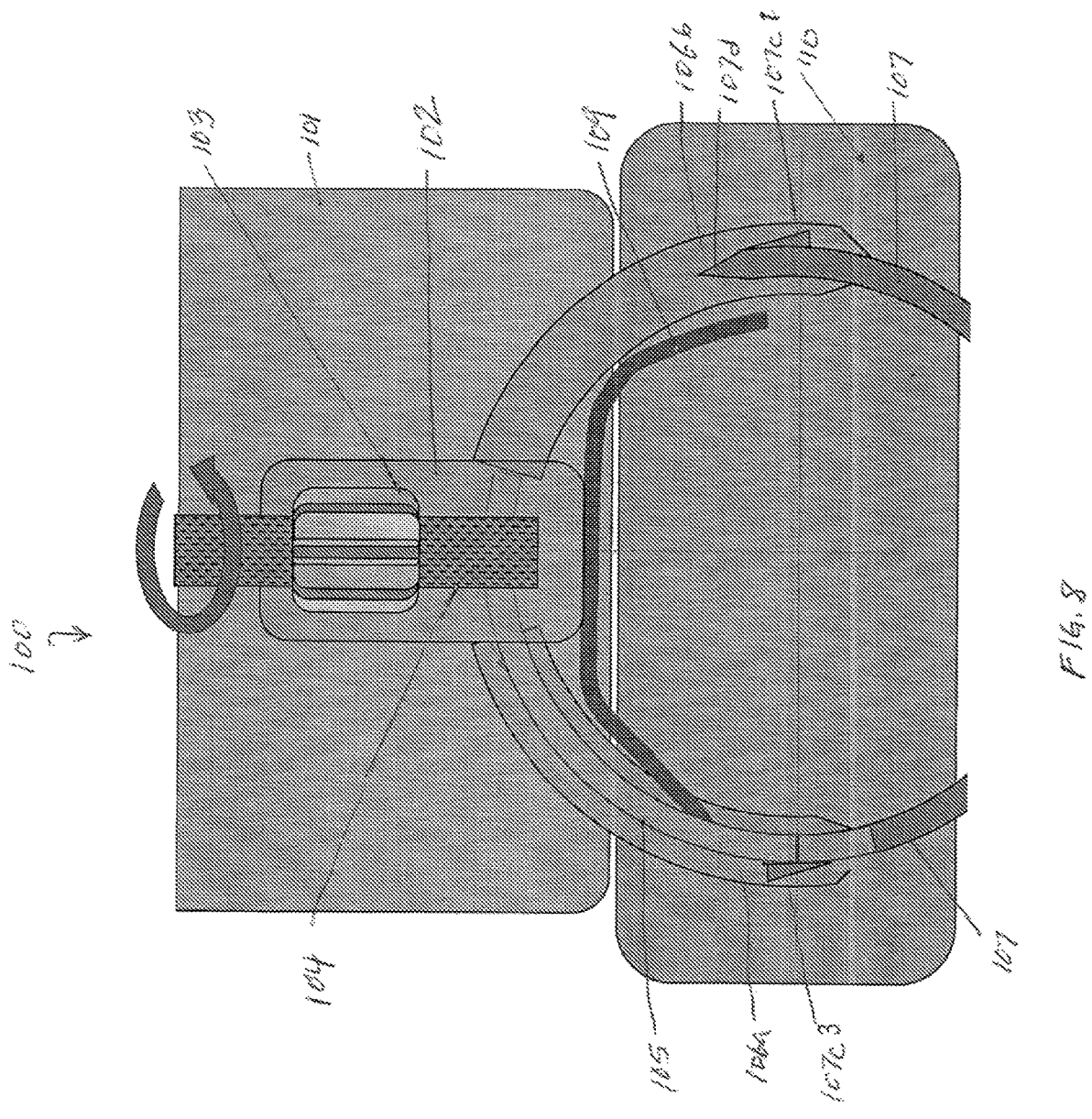

FIG. 8 is an illustration of a frontal view of the suturing device shown in FIG. 7. The wire rollers are rotated in the forward direction advancing the reciprocating shuttle 90 degrees to the second position of the reciprocating shuttle, driving the tip of the suturing needle back into the sleeve.

Figure 9:
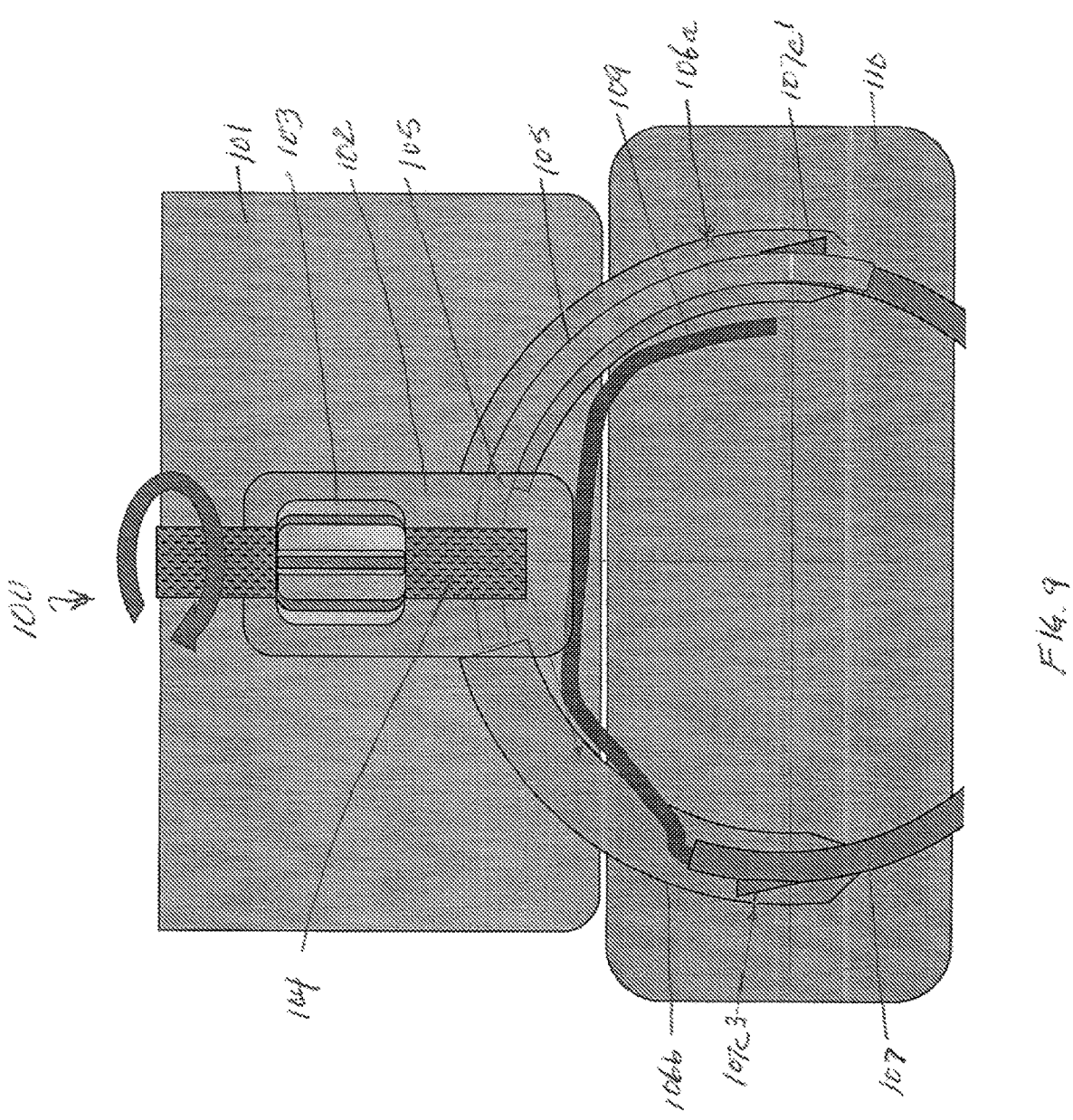

FIG. 9 is an illustration of a frontal view of the suturing device shown in FIG. 8. The wire rollers are rotated in the backward direction, moving the reciprocating shuttle back 90 degrees to the initial position of the reciprocating shuttle, with the tip of the suturing needle remaining in place the sleeve.

Figure 10:
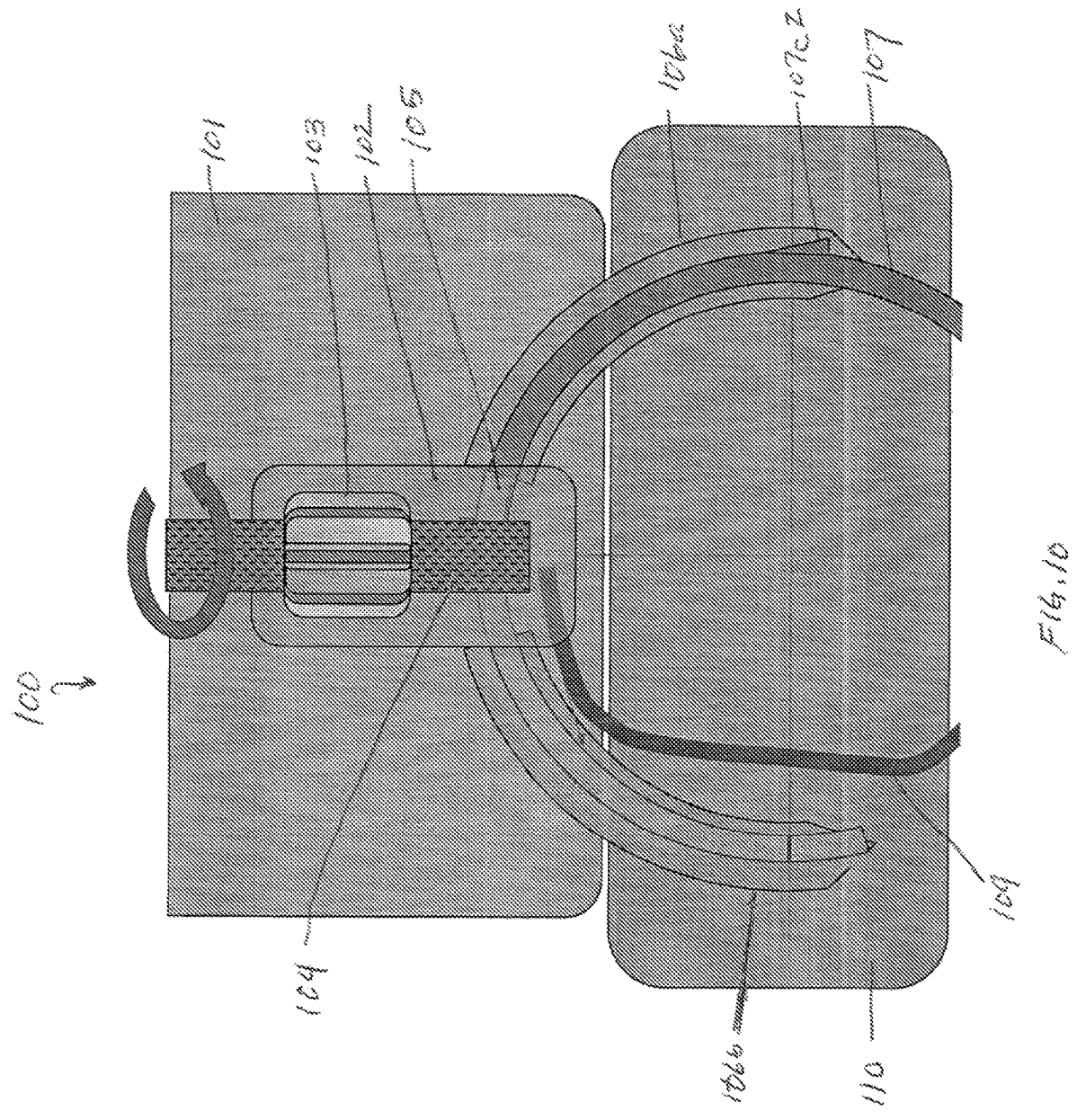

FIG. 10 is an illustration of a frontal view of the suturing device shown in FIG. 9. The wire rollers are rotated in the forward direction advancing the reciprocating shuttle 90 degrees to the second position of the reciprocating shuttle, driving the suture needle further back into the sleeve.

Figure 11:
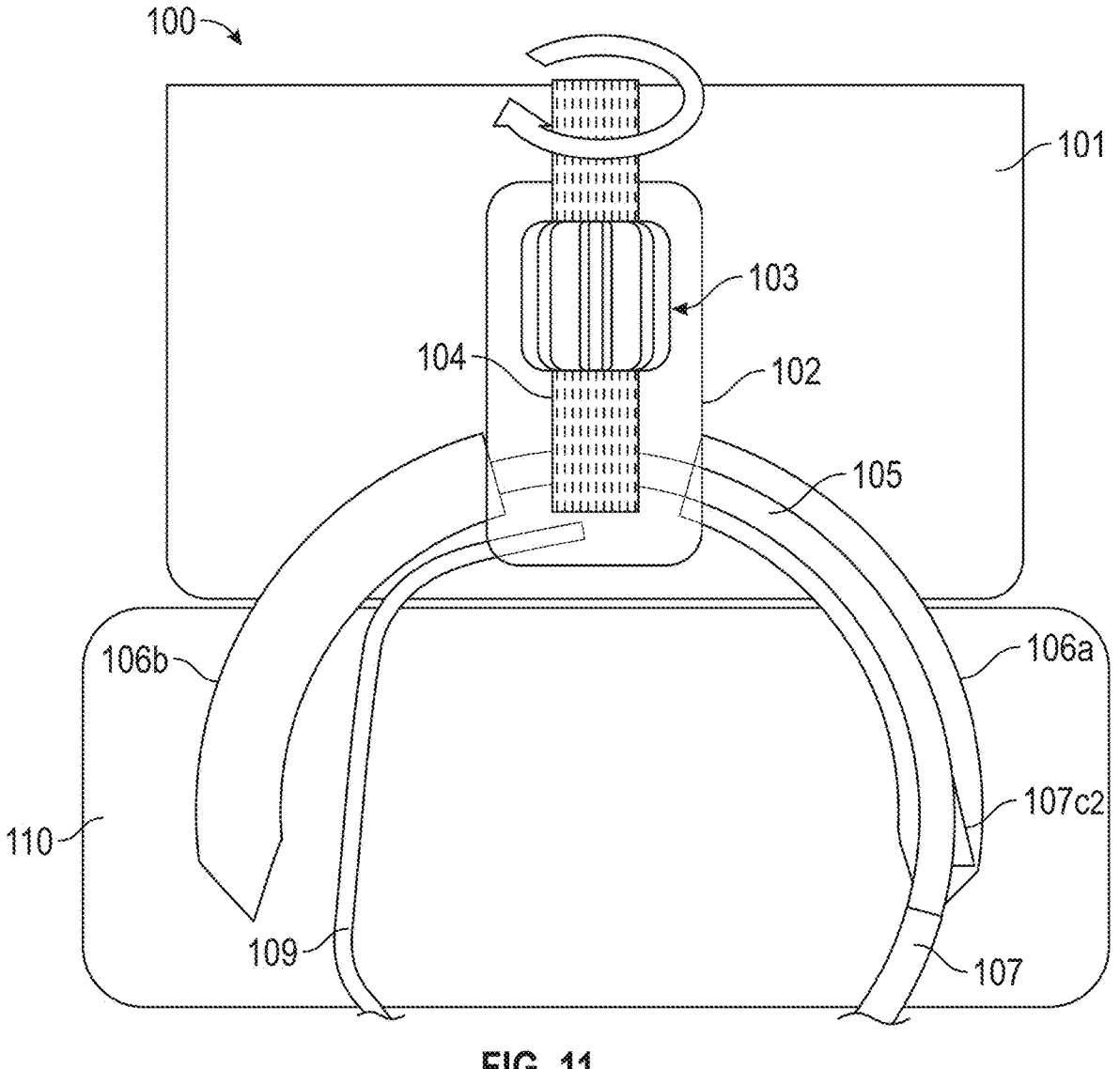

FIG. 11 is an illustration of a frontal view of the suturing device shown in FIG. 10. The wire rollers are rotated in the backward direction, moving the reciprocating shuttle back 90 degrees to the initial position of the reciprocating shuttle, with the tip of the suturing needle remaining in place in the sleeve.

Figure 12:
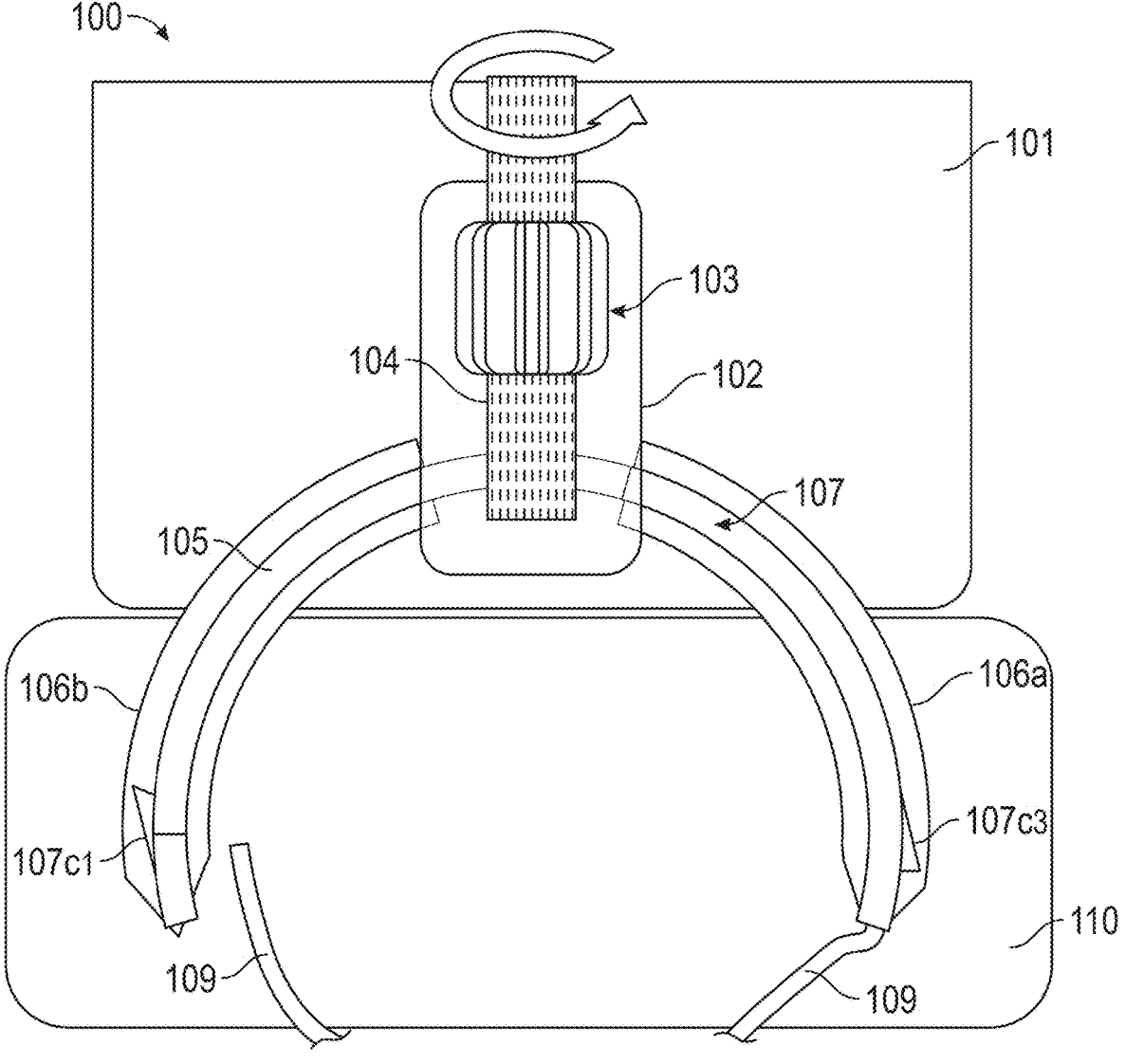

FIG. 12 is an illustration of a frontal view of the suturing device shown in FIG. 11. The wire rollers are rotated in the forward direction advancing the reciprocating shuttle 90 degrees to the second position of the reciprocating shuttle, driving the suture needle back to its original position in the sleeve.

Figure 13:
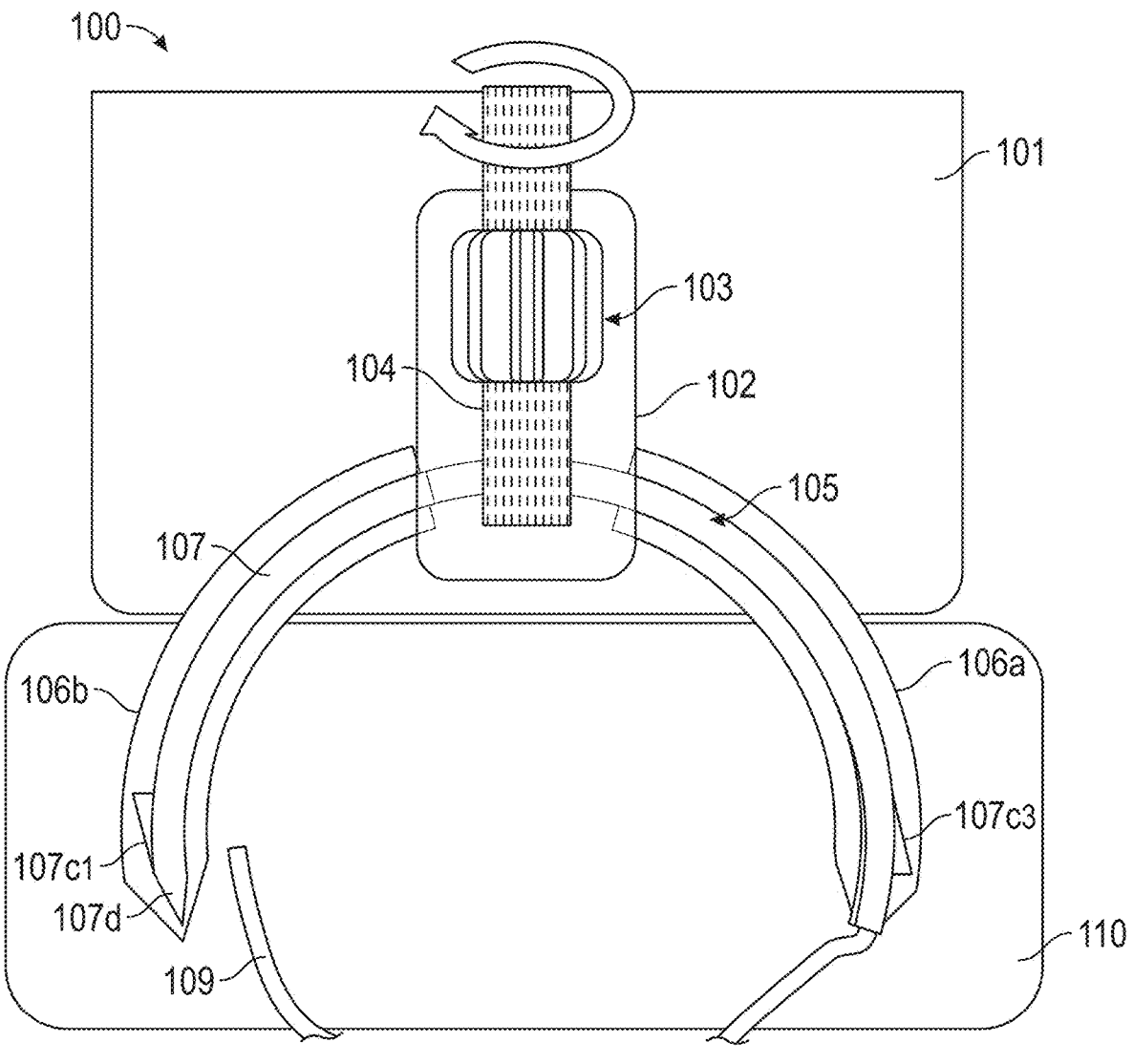

FIG. 13 is an illustration of a frontal view of the suturing device shown in FIG. 12. The wire rollers are rotated in the backward direction, moving the reciprocating shuttle back 90 degrees to the initial position of the reciprocating shuttle, with the tip of the suturing needle remaining in its initial position in the sleeve.

DETAILED DESCRIPTION

To provide an overall understanding of the disclosure, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

As used in the specification and claims, the singular forms "a", "an" and "the" include plural references unless the context clearly dictates otherwise. For example, the term "material" may include a plurality of materials unless the context clearly dictates otherwise. As used in the specification and claims, singular names or types referenced include variations within the family of said name unless the context clearly dictates otherwise.

Certain terminology is used in the following description for convenience only and is not limiting. The words "lower," "upper," "bottom," "top," "front," "back," "left," "right" and "sides" designate directions in the drawings to which reference is made, but are not limiting with respect to the orientation in which the various parts of the needle drivers or any assembly of them may be used.

This disclosure describes a device that allows movement of a curved member that has a semicircular structure and extends greater than 90 degrees and that is positioned in a fixed sleeve, through the sleeve and through tissue or other material. The curved member moves through the fixed sleeve which is semicircular and extends greater than 180 degrees. The fixed sleeve guides the curved member though a 360 degree rotation through the fixed sleeve. The curved member includes a nose (tip) and a tail. The nose is pointy and can pierce the tissue or material. At the tail or near the tail, a suture or string is connected. In certain embodiments, the curved member is a needle.

The fixed sleeve has a first tip and a second tip. Each of the first tip and the second tip are pointy or sharp and can pierce tissue or other material.

The movement of the curved member is enabled or caused by the rotation of a knob coupled to a shaft. The shaft runs from a handle portion of the device, where the knob is located or positioned to a gear mechanism located adjacent to the fixed sleeve. The gear element either directly or indirectly moves the curved member, as further described in the attachment hereto.

In certain embodiments, the shaft drives a structure that in turns drives the curved member. This would be indirect because the shaft is not driving the needle but rather it is driving an intervening structure. The intervening structure may serve to transmit a force to the curved member. In certain embodiments the system uses a reciprocating shuttle (or ferry) that can travel back and forth along a fixed or predetermined path. The shuttle can be made of a non-ferromagnetic metal. It would engage features in the curved member, which, in certain embodiment is a magnetized stainless steel needle. The engagement occurs at different points in a repeatable manner and acts as a ratchet. The needle remains in place while the shuttle moves because the needle is magnetized and held with magnetic force to the inner surface of the fixed sleeve. The fixed sleeve is comprised of curved, hollow, magnetized stainless steel tubes on either side of the shaft, and further comprises sharp tips. The fixed sleeve having an inner diameter large enough to accommodate the needle and shuttle. The curved, hollow, magnetized stainless steel tubes function like a pitchfork, piercing through tissue, fabric, or other material when pushed against it.

Some suturing devices can be used for medical purposes (e.g., suturing). For example, some of these devices can be used in transcatheter suturing, transcatheter intracardiac (or another body organ) suturing, and other flexible platform applications (e.g., endoscopic suturing, colonoscopic suturing). Some examples of surgeries where some of these suturing devices can be employed include laparoscopic surgery, robotic surgery, video-assisted or unassisted thoracoscopic surgery, arthroscopic surgery, natural orifice surgery, endoscopic surgery, gynecologic surgery, cardiac surgery, colorectal surgery, pulmonary surgery, gastric bypass surgery, hysterectomy surgery, dental surgery, urological surgery, brain surgery, or bariatric surgery, or among many others in human (e.g., between newborn until 120 years old, male, female) or animal (e.g., mammal, birds, fish, land animals) applications.

Note that some of these suturing devices can be employed in medical or non-medical settings, whether on an object is animate or inanimate. For example, the object, when animate, can include a tissue, an organ, a body part, whether of human or animal, or others. For example, the tissue can be a muscle tissue, a bone tissue, a nerve tissue, an organ tissue, or others. For example, the object, when inanimate, can include a medical device, a prosthesis, an implantable, a machine, a surgical instrument, or others. For example, some of the non-medical setting can include garment making, fabric stitching, knot applications, sewing, shoe making, or others.

Figure 1:
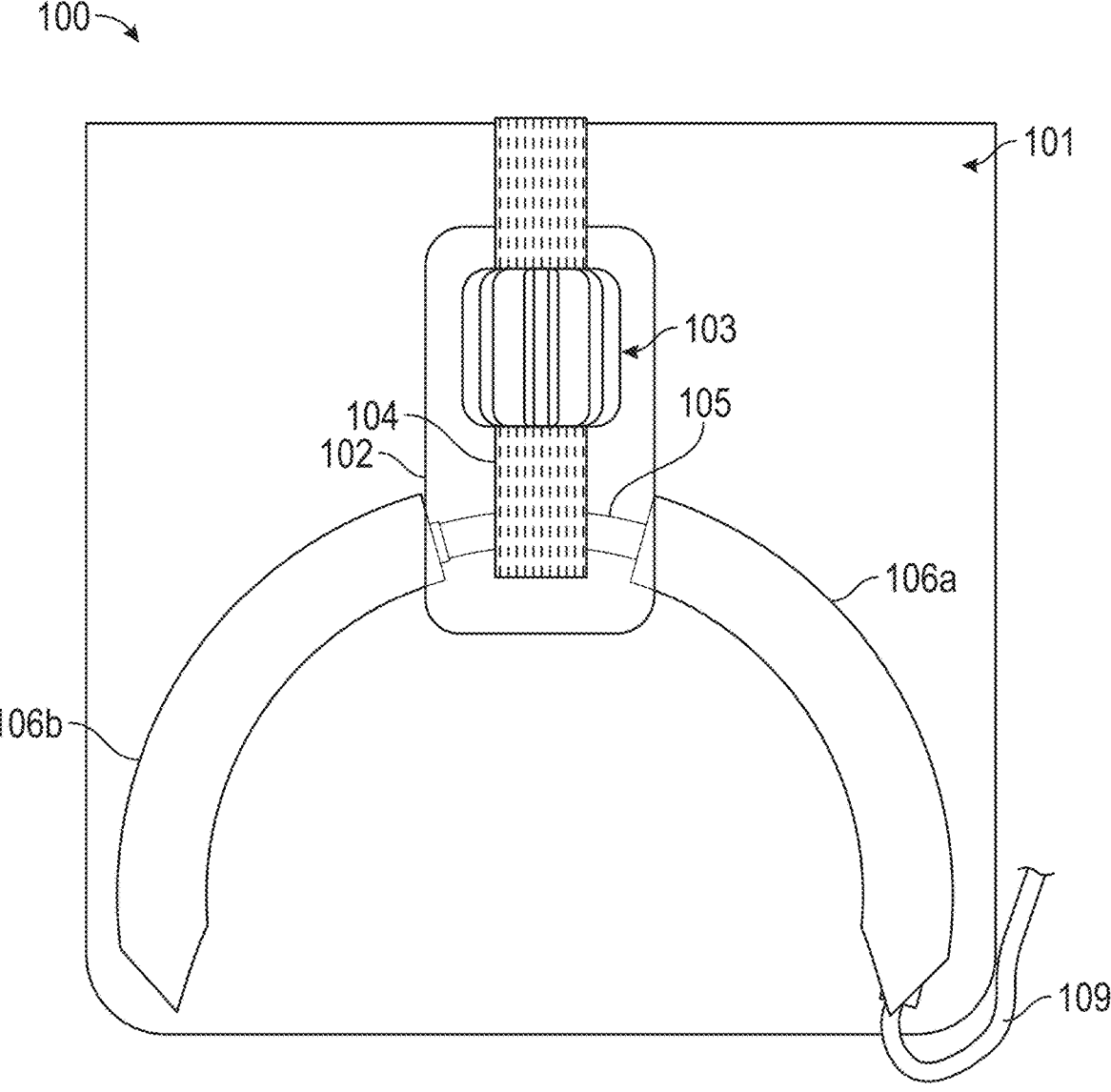
FIG. 1 is an illustration of a frontal view of a suturing device according to one embodiment of the present disclosure.

As shown in FIG. 1, the suturing device 100 is placed into a catheter 101. The suturing device 100 comprises a housing 102 with roller gears 103 and wire rollers 104 that extend out of the housing 102 and up the catheter 101 to a handle (not shown) with a knob (not shown) that can rotate the wire rollers 104 forward and backward. The suturing device 100 also comprises a sleeve having a first magnetized tube 106a and a second magnetized tube 106b on either side of housing 102 the sleeve contains a reciprocating shuttle 105 and a needle 107 (not visible in this figure). Suture thread 109 is attached to the rear end of needle 107 (not visible in this figure), and goes inside the catheter (shown outside the catheter for simplicity).

As shown in the side view in FIG. 2, the housing 102 comprises two roller gears 103 that are engaged and controlled by two wire rollers 104, and an opening 108 for a suture thread 109 to pass through. Also shown are reciprocating shuttle 105 and needle 107 with fin 107c. While needle 107 is magnetized, housing 102, roller gears 103 and wire rollers 104 are not magnetic, and can be comprised of any not magnetic or magnetized metal or metal alloy. The reciprocating shuttle 105 is made from non-ferromagnetic metal.

As shown in FIG. 3, a cross-section view of the tissue-piercing needle 107 with outer circumference 107a, inner circumference 107b, and fin 107c. Also shown is opening 108 and suture thread 109 attached to needle 107.

FIG. 4A shows the needle 107 having in the front end needle tip 107d, and front fin 107c1, middle fin 107c2 and rear fin 107c placed at about 90 degrees from each other, and reciprocating shuttle 105 having a front window 105a and a rear window 105b. Also shown is suture thread 109 attached to the rear end of needle 107 (not visible in this figure). FIG. 4B shows a cross-section view of the reciprocating shuttle 105 in front of the front window 105a showing needle 107 and needle fin 107c covered partially by the front window 105a. It is also seen that reciprocating shuttle 105 is completely open on its inner circumference side. FIG. 4C shows a cross-section view of the reciprocating shuttle 105 at the front window 105a showing needle 107 and fin 107c. It is once again seen that reciprocating shuttle 105 is completely open on its inner circumference side.

The needle tip portion 107d of the curved suture needle 107 may be a tapered tip wherein the needle tip portion is round and tapers smoothly to a point. Alternatively, the needle tip portion 107d may be triangular, and may have a sharpened cutting edge on the inside or on the outside, or may have a "trocar point" or "tapercut" whereby the needle body is round and tapered, but ends in a small triangular cutting point. Alternatively, the needle tip 107*d* may be a blunt point, such as for suturing friable tissues, or may have a needle tip portion that includes "side cutting" or "spatula points" whereby the needle is flat on top and bottom with a cutting edge along the front to one side (these are typically used for eye surgery).

The material configuring the suture needle 107 is not limited, and may comprise any metal or a metal alloy that is magnetic or magnetizable. Other processes when forming or finishing the needle may be siliconization, coating with any number or combination of biocompatible coating materials or lubrication with any number or combination of biocompatible lubricating agents, among other processes.

FIG. 5 shows a cross-section of the suturing device 100 in catheter 101 as it is inserted into the tissue or textile to be sutured 110. Shown is housing 102 containing roller gears 103 and wire roller 104 and portion of sleeve comprising first magnetized tube 106*a* and second magnetized tube 106*b*. The roller gears 103 transmit force from one roller to the other, allowing the use of only one driving wire down the catheter. First magnetized tube 106*a* and second magnetized tube 106*b* have pointed tips that serve to penetrate or pierce the tissue or textile to be sutured. First magnetized tube 106*a* has a longitudinal slit (not seen in this figure) running along its inner circumference for free suture movement. Reciprocating shuttle 105 is in its initial position with the front window (105*a*—not seen in this figure) over the middle fin (107*c*2—not visible in this figure) of the needle 107 and back window (105*b*—not seen in this figure) over the back fin 107*c*3 of the needle 107 and contained in the first magnetized tube 106*a*. Also shown are suture needle 107 with front fin 107*c*1 contained inside first magnetized tube 106*a* and second magnetized tube 106*b*, and constrained by the reciprocating shuttle 105. Needle 107 has an arc of about 210 degrees, and both magnetized tubes 106*a* and 106*b* together also make up an arc of about 210 degrees. Suture thread 109 is attached to the rear end of needle 107, and is contained within the catheter 101 (shown outside the catheter for simplicity). The device 100 is designed to have the wire rollers 104 move the reciprocating shuttle in 90 degrees or arc in either direction (on the forward or backward stroke) at a time. The device 100 is also designed to allow penetration of the pointed ends of the magnetic tubes 106*a* and 106*b* beyond the equator of the circle, maximizing the tissue depth even before deploying the suture needle 107.

FIG. 6 shows the next step in suturing. Shown is suturing device 100 in catheter 101 as roller gears 103 turn in the forward direction, which turns the wire rollers 104 forward advancing the reciprocating shuttle 105 by 90 degrees to the second position, with the front window 105*a* still over the middle fin 107*c*2 of the needle 107, which in turn drives the needle tip (107*d*—not visible in this drawing) by 90 degrees further into the tissue 110 beyond the pointed end of one of the hollow, magnetized tube 106*b* (shown in cross-section). The suture thread 109 is attached to the rear end of the needle (107—not visible in this drawing), which is contained inside the hollow magnetized tube 106*a* and constrained by the reciprocating shuttle 105.

FIG. 7 shows the next step in suturing. Shown is suturing device 100 in catheter 101 as roller gears 103 turn in the backward direction, which turns the wire rollers 104 backward reversing the reciprocating shuttle 105 by 90 degrees to the initial position, with the front window 105*a* now over the back fin 107*c*3 of the needle 107. This movement does not retract the needle 107 or the needle tip (107*d*—not visible in this drawing) by 90 degrees because the magnetized needle 107 is held in place by the hollow, magnetized tube 106*b*. The suture thread 109 is attached to the rear end of the needle (107—not visible in this drawing), which is contained inside the hollow magnetized tube 106*a* and constrained by the reciprocating shuttle 105.

FIG. 8 shows the next step in suturing. Shown is suturing device 100 in catheter 101 as roller gears 103 turn in the forward direction, which turns the wire rollers 104 forward advancing the reciprocating shuttle 105 by 90 degrees to the second position, with the front window 105*a* now over the back fin 107*c*3 of the needle 107 inside of magnetized hollow tube 106*b* (shown in cross-section), which in turn drives the needle tip 107*d* by 90 degrees further to now place the front fin 107*c*1 and needle tip 107*d* into the hollow, magnetized tube 106*a*. The suture thread 109 is attached to the rear end of the needle (107—not visible in this drawing), which is contained inside the hollow magnetized tube 106*a* and constrained by the reciprocating shuttle 105. Because both the suture needle 107 and the sleeve assembly (comprising magnetized hollow tubes 106*a* and 106*b*) have an arc of 210 degrees there are 30 degrees of overlap on each side when the suture needle is at its most exposed configuration. The suture needle is always magnetically held at some point against hollow magnetized tube 106*a* or magnetized hollow tube 106*b*.

FIG. 9 shows the next step in suturing. Shown is suturing device 100 in catheter 101 as roller gears 103 turn in the backward direction, which turns the wire rollers 104 backward reversing the reciprocating shuttle 105 by 90 degrees to the initial position, with the front window 105*a* now empty and the back window 105*b* over the front fin 107*c*1 of the needle 107, which is constrained by the reciprocating shuttle 105. This movement does not retract the needle 107, the front fin 107*c*1 or the needle tip (107*d*—not visible in this drawing) by 90 degrees because the magnetized needle 107 is held in place by both hollow, magnetized tubes 106*b* and 106*a*. The suture thread 109 is attached to the rear end of the needle 107, which is contained inside the hollow magnetized tube 106*b*.

FIG. 10 shows the next step in suturing. Shown is suturing device 100 in catheter 101 as roller gears 103 turn in the forward direction, which turns the wire rollers 104 forward advancing the reciprocating shuttle 105 by 90 degrees to the second position, with the front window 105*a* now empty and the rear window over the front fin 107*c*1 of the needle 107 (not visible in this drawing), which in turn drives the needle tip 107*d* by 90 degrees further to now go further into and through the hollow, magnetized tube 106*a*, which now contains the middle fin 107*c*2 of needle 107. The suture thread 109 is attached to the rear end of the needle (107—not visible in this drawing), which is contained in the tissue to be sutured 110. The suture needle is magnetically held against hollow magnetized tube 106*a*.

FIG. 11 shows the next step in suturing. Shown is suturing device 100 in catheter 101 as roller gears 103 turn in the backward direction, which turns the wire rollers 104 backward reversing the reciprocating shuttle 105 by 90 degrees to the initial position, with the front window 105*a* now over the front fin and the back window 105*b* over the middle fin 107*c*2 of the needle 107, which is constrained by the reciprocating shuttle 105. This movement does not retract the needle 107 or the needle tip (107*d*—not visible in this drawing) by 90 degrees because the magnetized needle 107 is held in place by hollow, magnetized tube 106*a*. The suture thread 109 is attached to the rear end of the needle 107 (not visible in this drawing).

FIG. 12 shows the next step in suturing. Shown is suturing device 100 in catheter 101 as roller gears 103 turn in the forward direction, which turns the wire rollers 104 forward advancing the reciprocating shuttle 105 by 90 degrees to the second position, with the front window 105a now over the front fin 107c1 and the rear window over the middle fin 107c2 of the needle 107 (not visible in this drawing), which in turn drives the needle tip 107d (not visible in this drawing) by 90 degrees further to now go further into the hollow, magnetized tube 106b, and moves the rear fin 107c into hollow, magnetized tube 106a. The suture thread 109 is attached to the rear end of the needle 107, which is contained in the hollow magnetized tube 106a.

FIG. 13 shows the next step in suturing. Shown is suturing device 100 in catheter 101 as roller gears 103 turn in the backward direction, which turns the wire rollers 104 backward reversing the reciprocating shuttle 105 by 90 degrees to the initial position, with the front window 105a now over the middle fin 107c2 (not visible in this drawing) and the back window 105b over the back fin 107c3 of the needle 107, which is constrained by the reciprocating shuttle 105. This movement does not retract the needle 107 or the needle tip 107d or the front fin 107c1 by 90 degrees because the magnetized needle 107 is held in place by hollow, magnetized tubes 106a and 106b. The suture thread 109 is attached to the rear end of the needle 107. The needle 107 has now made a full 360 degree revolution, and both the needle 107 and the reciprocating shuttle are in their original starting positions. The suturing device 100 is now ready to be retracted from the tissue 110 and moved to the next portion of the tissue to be sutured.

According to certain embodiments, a suture thread 109 may be swaged to the rear end of the needle 107 by a thread attachment portion. That is, the needle 107 is generally an atraumatic needle, i.e., eyeless needle 107, having a suture material or thread 109 attached at an end by swaging whereby the suture material 109 is inserted into a channel at the blunt end of the needle 107, such as into a thread attachment portion, which is then deformed to a final shape to hold the suture 109 and needle 107 together. The needle 107 may be permanently swaged to the suture material 109 or may be designed to come off the suture material 109 with a sharp straight tug. These "pop-offs" are commonly used for interrupted sutures, where each suture is only passed once and then tied.

The suture material or thread 109 may be monofilamentary, i.e., formed of a single filament, or multifilamentary, i.e., formed from a combination of two or more filaments, e.g., three filaments arranged in a braided fashion. The suture thread 109 has a length, where that length is typically at least 5 inches, or at least 10 inches, or at least 15 inches, or at least 20 inches. The suture thread 109 will typically have two ends, which may be described as a deployment end and/or a trailing end. In such a case, the deployment end of the suture thread 109 is that end that first enters tissue, adjacent to the needle 107, such as connected via a thread attachment portion to the rear end of the trunk portion of the needle 107. Alternatively, the suture material 109 may be looped, such that each of the two free ends are connected to the needle 107 by the thread attachment portion.

The suture thread 109 can be a suture, which can be non-absorbable or absorbable of various gauges. The suture thread 109 can include silk, cotton, fabric, nylon, polyester, silver, copper, Dacron, rubber, silicon, plain or chromic catgut, polyglycolide, polydioxanone, monocryl, polypropylene, triclosan, caprolactone, polymer, glycolide, I-lactide, p-dioxanone, trimethylene carbonate, ε-caprolactone, stainless steel, ceramic, glass, leather, or other natural or artificial materials. The suture thread 109 is solid, but can be perforated. The suture thread 109 is internally dense, but can be hollow. The thread 109 can have a cross-section that is closed-shaped (e.g., O-shape, D-shape, O-shape, square, rectangle, triangle, polygon) or open-shaped (e.g., U-shape, C-shape, V-shape), whether symmetrical or asymmetrical.

The suture material or thread 109 may be bioabsorbable, such that after introduction into a tissue it is broken down and absorbed by the body. Typically, the degradation process is at least partially mediated by, or performed in, a biological system. Accordingly, bioabsorbable refers to a chain scission process by which a polymer chain is cleaved through various mechanisms, including, for example, by chemical reaction (e.g., hydrolysis, oxidation/reduction, enzymatic mechanisms or a combination of these) or by a thermal or photolytic process. Bioabsorbable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™[glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). In certain embodiments, the bioabsorbable suture material may comprise or include any other polymer useful for suturing applications that currently exists or that may be developed in the future.

Alternatively, the suture material or thread 109 may be non-degradable, such that it is not degraded by chemical, thermal, or photolytic process. Non-degradable suture material includes polyamide (also known as nylon, such as nylon 6 and nylon 6.6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are particularly suitable for applications in which the suture is meant to remain permanently or is meant to be physically removed from the body. In certain embodiments, the non-degradable suture material may comprise or include any other polymer useful for suturing applications that currently exists or that may be developed in the future.

The suture material or thread 109 may comprise a coating or agent applied to a surface thereof that may affect would healing, such as a coating material, wound healing agent, antimicrobial agent, antibacterial agent, growth factor, adhesive, sealant, blood product, blood component, preservative, anti-adhesive, protein, polysaccharide, peptide, genetic material, viral vector, nucleic acid, nucleotide, plasmid, lymphokine, radioactive agent, metal, alloy, salt, growth factor, growth factor antagonist, cell, hydrophobic agent, hydrophilic agent, immunological agent, anti-colonization agent, and combinations thereof. The suture material or thread 109 may comprise a coating or agent applied to a surface thereof that may enhance the surgeon's ability to accurately suture, such as colorants, dyes, ultraviolet absorbers, ultraviolet stabilizers, photochromic agents, diagnostic agent, imaging agent, radiopaque agent, or combinations thereof.

Suture sizing is based upon diameter. The United States Pharmacopeia ("USP") designation of suture size runs from 0 to 7 in the larger range and 1-0 to 11-0 in the smaller range;

in the smaller range, the higher the value preceding the hyphenated zero, the smaller the suture diameter. Under the USP nomenclature system, the actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the suture materials for use with the suture needles disclosed herein include without limitation 7, 6, 5, 4, 3, 2, 1, 0, 1-0, 2-0, 3-0, 4-0, 5-0, 6-0, 7-0, 8-0, 9-0, 10-0 and 11-0. It is to be understood that a variety of suture lengths may be used with the suture needles described herein.

Features or functionality described with respect to certain example embodiments may be combined and sub-combined in and/or with various other example embodiments. Also, different features and/or elements of example embodiments, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, can be at least partially performed via at least one entity or actor in any manner.

As used herein, a term "about" or "substantially" refers to a variation from a nominal value/term, such as, for example up to a +/−10% variation, or a plus or minus 1%, 2%, 3%, 4%, 5%, 6%, 7%, 8%, 9%, or 10% variation. Such variation is always included in any given value/term provided herein, whether or not such variation is specifically referred thereto.

Any component described herein can include a material suitable for a medical use. The material can be, flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

The device and system of the present disclosure has been described with specific reference to certain drawings and various embodiments, but may, however, be embodied in many different forms and should not be construed as necessarily being limited to only embodiments disclosed herein. Rather, these embodiments are provided so that this disclosure is thorough and complete, and fully conveys various concepts of this disclosure to skilled artisans.

Note that various terminology used herein can imply direct or indirect, full or partial, temporary or permanent, action or inaction. For example, when an element is referred to as being "on," "connected" or "coupled" to another element, then the element can be directly on, connected or coupled to the other element or intervening elements can be present, including indirect or direct variants. In contrast, when an element is referred to as being "directly connected" or "directly coupled" to another element, there are no intervening elements present.

Likewise, as used herein, a term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

Similarly, as used herein, various singular forms "a," "an" and "the" are intended to include various plural forms as well, unless context clearly indicates otherwise. For example, a term "a" or "an" shall mean "one or more," even though a phrase "one or more" is also used herein.

Moreover, terms "comprises," "includes" or "comprising," "including" when used in this specification, specify a presence of stated features, integers, steps, operations, elements, or components, but do not preclude a presence and/or addition of one or more other features, integers, steps, operations, elements, components, or groups thereof. Furthermore, when this disclosure states that something is "based on" something else, then such statement refers to a basis which may be based on one or more other things as well. In other words, unless expressly indicated otherwise, as used herein "based on" inclusively means "based at least in part on" or "based at least partially on."

Additionally, although terms first, second, and others can be used herein to describe various elements, components, regions, layers, or sections, these elements, components, regions, layers, or sections should not necessarily be limited by such terms. Rather, these terms are used to distinguish one element, component, region, layer, or section from another element, component, region, layer, or section. As such, a first element, component, region, layer, or section discussed below could be termed a second element, component, region, layer, or section without departing from this disclosure.

Also, unless otherwise defined, all terms (including technical and scientific terms) used herein have the same meaning as commonly understood by one of ordinary skill in an art to which this disclosure belongs. As such, terms, such as those defined in commonly used dictionaries, should be interpreted as having a meaning that is consistent with their meaning in a context of a relevant art and should not be interpreted in an idealized or overly formal sense unless expressly so defined herein.

In addition, features described with respect to certain example embodiments may be combined in or with various other example embodiments in any permutational or combinatory manner. Certain features or elements of example embodiments, as disclosed herein, may be combined in a similar manner. The term "combination", "combinatory," or "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

Although preferred embodiments have been depicted and described in detail herein, skilled artisans know that various modifications, additions, substitutions and the like can be made without departing from spirit of this disclosure. As such, these are considered to be within the scope of the disclosure, as defined in the following claims.

The invention claimed is:

1. A device comprising:
   a) a housing with a top end and a bottom end, and a first side and a second side, wherein the bottom end of the housing defines an opening;
   b) a first rotatable shaft with a first end and a second end, the first rotatable shaft coupled to a first roller gear proximal to the second end of the first rotatable shaft, the first roller gear and the second end of the first rotatable shaft positioned in the housing;
   c) a second rotatable shaft with first end and a second end, the second rotatable shaft coupled to a second roller gear proximal to the second end of the second rotatable shaft, the second roller gear and the second end of the second rotatable shaft positioned in the housing, wherein the first roller gear engages the second roller gear;
   d) a sleeve comprising a first curved, hollow, stainless steel, magnetized tube having a first end and a second end, the first end of the first tube having a first sharp tip, wherein the second end of the first tube is positioned on the first side of the housing, and a second curved, hollow, stainless steel, magnetized tube having a first end and a second end, the first end of the second tube having a second sharp tip, wherein the second end of the second tube is positioned on the second side of the housing;
   e) a reciprocating shuttle positioned in the sleeve; and
   f) a curved stainless steel, magnetized needle, positioned in the sleeve, wherein the sleeve having an inner diameter large enough to accommodate the needle and the shuttle, and wherein the shuttle is positioned between the sleeve and the needle, wherein the shuttle engages the needle, wherein the shuttle is coupled to the first and second rotatable shaft, and wherein a rotation of the first and second rotatable shaft moves the shuttle through the sleeve which in turn drives the needle through the sleeve.

2. The device of claim 1, wherein the needle comprises a first end, a second end and a middle portion, wherein the first end has a sharp tip and the second end is coupled to a suture.

3. The device of claim 2, wherein the needle comprises a plurality of fins.

4. The device of claim 3, wherein the needle comprises a first fin located proximal to the first end of the needle, a second fin proximal to the middle portion of the needle, and a third fin proximate to the second end of the needle.

5. The device of claim 4, wherein the second fin is located approximately 90 degrees from the first and third fins.

6. The device of claim 4, wherein the shuttle has a first end and a second end, and a first window proximal to the first end and a second window proximal to the second end.

7. The device of claim 6, wherein the shuttle engages the needle via the interaction of the first or second window with the first, second or third fin.

8. The device of claim 1, wherein the sleeve is semicircular and extends greater than 180 degrees.

9. The device of claim 8, wherein the sleeve extends 210 degrees.

10. The device of claim 1, wherein the sleeve guides the needle through a 360 degree rotation through the sleeve.

11. The device of claim 1, wherein the needle is semicircular and extends greater than 180 degrees.

12. The device of claim 10, wherein the needle extends 210 degrees.

13. The device of claim 1, further comprising a knob coupled to either the first roller gear or the second roller gear.

14. The device of claim 13, further comprising a handle coupled to the knob.

15. A method for suturing tissue, comprising the steps of:
   a) providing a device comprising:
      i) a handle;
      ii) a housing with a top end and a bottom end, and a first side and a second side, wherein the bottom end of the housing defines an opening;
      iii) a rotatable shaft with a first end and a second end, the rotatable shaft coupled to a first roller gear proximal to the second end of the rotatable shaft, the first roller gear and the second end of the rotatable shaft positioned in the housing, the rotatable shaft coupled to the handle;
      iv) a second roller gear positioned in the housing and engaged with the first roller gear;
      v) a sleeve comprising a first curved, hollow, stainless steel, magnetized tube and a second curved, hollow, stainless steel, magnetized tube, wherein the first tube is positioned on a first side of the shaft and the second tube is positioned on a second side of the shaft, wherein the first tube comprises a first sharp tip and the second tube comprises a second sharp tip;
      vi) a reciprocating shuttle; and
      vii) a curved stainless steel, magnetized needle, positioned in the sleeve, wherein the sleeve having an inner diameter large enough to accommodate the needle and the shuttle, and wherein the shuttle is positioned between the sleeve and the needle, wherein the shuttle engages the needle, wherein the shuttle is coupled to the shaft, and wherein a rotation of the shaft moves the shuttle which in turn drives the needle through the sleeve;
   b) positioning the needle at an initial position in the sleeve;
   c) piercing the tissue with the sleeve;
   d) actuating the rotatable shaft in the forward direction to advance the shuttle in the first tube of the sleeve which advances the needle into the tissue;
   e) actuating the rotatable shaft in the opposite direction to retract the shuttle into the second tube of the sleeve;
   f) repeating steps c) and d) until the needle is positioned in the initial position within the sleeve; and
   g) repeating steps b) through e) until completion of the suturing process.

16. The method of claim 15, further comprising a knob in communication with either the first roller gear or the second roller gear, the knob coupled to the handle.

* * * * *